United States Patent [19]

Smith et al.

[11] Patent Number: 5,702,925

[45] Date of Patent: Dec. 30, 1997

[54] NUCLEOSIDE ANALOGUE METHOD

[75] Inventors: Clifford Smith, Tring, United Kingdom; Carl Fuller, Cleveland Heights, Ohio

[73] Assignee: Amersham International PLC, Buckinghamshire, United Kingdom

[21] Appl. No.: 649,599

[22] PCT Filed: Dec. 1, 1994

[86] PCT No.: PCT/GB94/02630

§ 371 Date: May 24, 1996

§ 102(e) Date: May 24, 1996

[87] PCT Pub. No.: WO95/15395

PCT Pub. Date: Jun. 8, 1995

[30] Foreign Application Priority Data

Dec. 1, 1993 [EP] European Pat. Off. ............ 93309597

[51] Int. Cl.$^6$ ..................... C12P 19/34; C12N 11/00; C07H 21/02; C07H 21/00
[52] U.S. Cl. ..................... 435/91.1; 435/174; 536/22.1; 536/25.32
[58] Field of Search ..................... 435/91.1, 174; 536/27.1, 25.32

[56] References Cited

U.S. PATENT DOCUMENTS 5,002,868  3/1991  Jacobson et al. ..................... 435/6

FOREIGN PATENT DOCUMENTS

WO 91/02090  2/1991  WIPO ..................... C12Q 1/68
WO 93/24655  12/1993  WIPO ..................... C12Q 1/68

OTHER PUBLICATIONS

Fontanel et al. P32 Labeling of nonnucleosidic moieties 5'-attached to oligonucleotides, Analytical Biochemistry vol. 214, No. 1, pp. 338–340, 1993.

Fontanel et al., "$^{32}$P Labeling of Nonnucleosidic Moieties 5'-Attached to Oligonucleotides," *Analytical Biochemistry* 214(1):338–340 (1993).

Meldrum et al., "Kinetics and Mechanism of DNA Repair. Preparation, Purification and Some Properties of Caged Dideoxynucleoside Triphosphates," *Chemical Abstracts* 112(23):313 (1990).

Wharton et al., "Kinetics and Mechanism of DNA Repair: An Automated Programmable Apparatus for Fast Time-Resolved Studies of the Repair of Mammalian DNA After UV Irradiation," *Biochemical Journal* 293(3):825–828 (1993).

Yousaf et al., "A New and Improved Method For 3'-end Labelling DNA Using [$\alpha$-$^{32}$P]ddATP," *Gene* 27(3):309–313 (1984).

*Primary Examiner*—Stephanie W. Zitomer
*Assistant Examiner*—Joyce Tung
*Attorney, Agent, or Firm*—Marshall, O'Toole, Gerstein, Murray & Borun

[57] ABSTRACT

A method is provided of making a dideoxynucleoside mono- or tri-phosphate, which is optionally 32-P or 33-P or 35-S radiolabelled which involves reacting the corresponding dideoxynucleoside with an optionally radiolabelled nucleotide phosphate or thiophosphate donor in the presence of a kinase of phosphotransferase enzyme which catalyses the reaction. A method of sequencing nucleic acids by a chain termination of a kinase or phosphotransferase enzyme which catalyses the reaction. A method of sequencing nucleic acids by a chain termination technique involves detecting the products of enzymatic synthesis by means of isotopically labelled chain terminating nucleotide analogues.

20 Claims, No Drawings

NUCLEOSIDE ANALOGUE METHOD

This application is filed under 35 USC 371 as the National Stage of PCT/GB94/02630, filed Dec. 1, 1994, now WO 95/15395, published Jun. 8, 1995 and has priority to EPO application Ser. No. 93309597.8 filed Dec. 1, 1993.

[$\alpha^{32}$P] dideoxyadenosinetriphosphate is commercially available. The current chemical production method is very inefficient. This invention provides an enzymatic method of preparation, which improves efficiency. The method is applicable to a wide range of compounds besides this one.

T4 polynucleotide kinase (T4 PNK) is usually associated with the phosphorylation of the 5'-OH group of an oligonucleotide, DNA or 2-deoxynucleoside-3-monophosphate (or ribo) by transfer of the gamma-phosphate group from ATP. (Analytical Biochemistry 214, 338–340, 1993). It is generally believed that for T4 PNK to phosphorylate the 5'-OH group of a nucleotide, the nucleotide must contain a 5'-OH and a 3'-phosphate group. Because the 3'-phosphate group is clearly absent from 2',3'-dideoxynucleosides and other known chain terminators, the use of T4 PNK to catalyse their phosphorylation has hitherto been considered impossible. This invention results from our surprising discovery that T4 PNK can be used to catalyse this reaction. The invention covers the use of T4 PNK and other enzymes to catalyse this and related reactions.

Known kits for sequencing nucleic acids comprise supplies of all four nucleotides, and supplies of all four 2',3'-dideoxynucleotides, and a supply of one nucleotide which has been labelled, generally radioactively labelled, to permit detection of the products after sequencing by electrophoresis. In another aspect, this invention is based on the realization that improved results can be obtained by radiolabelling the dideoxynucleotides.

Kits containing fluorescently labelled chain terminators (ddNTPs) are known but isotopically labelled ddNTPs have structures which are less likely to interfere with polymerase activity, gel mobility and do not require sophisticated equipment for detection.

In one aspect, this invention provides a method of making a nucleotide or nucleotide analogue or nucleotide adduct, having a 5'-phosphate or a 5'-thiophosphate group which method comprises reacting a starting nucleoside or nucleoside analogue or nucleoside adduct having a 5'-OH group but no 3'-phosphate group with a nucleotide phosphate or thiophosphate donor in the presence of an enzyme which catalyses the reaction. The nucleoside can be an unmodified ribo or deoxyribonucleoside e.g. 2' deoxyadenosine.

It is possible that the nucleoside, nucleoside analogue or nucleoside adduct may be non-labelled and that the phosphate donor is also non-labelled. This produces the corresponding nucleotide without the need to use chemical phosphorylating agents which may be damaging to the starting material in some circumstances.

Alternatively the nucleoside can be labelled with a detectable isotope e.g. a radioisotope such as for example $^3$H or $^{14}$C and then converted to the corresponding labelled nucleotide with a non-labelled phosphate donor or thiophosphate donor.

Preferably the nucleotide phosphate or thiophosphate donor is radiolabelled with a detectable isotope e.g. a radioactive isotope such as $^{32}$P or $^{33}$P or $^{35}$S, whereby the obtained nucleotide or nucleotide analogue or nucleotide adduct is radiolabelled by virtue of having a 5'-phosphate or 5'-thiophosphate group comprising $^{32}$P or $^{33}$P or $^{35}$S The term nucleoside analogue refers to a compound which is similar to a nucleoside and is capable of performing at least some of the biochemical functions of a nucleoside, and includes monomers and multimers. There follows a non-exhaustive list of nucleoside analogues.

Base Modifications
    2-aminoadenosine
    5-bromocytosine
    5-methylcytosine
    5-(1-propynyl)cytosine
    5-(1-propynyl)uracil
    5-aminoallyluracil
    5-aminoallyluracil-"label"
    thiouracil/thiothymine/thioguanine
    aziridene derivatives Sugar Modifications
    2'-O-alkyl (e.g. allyl or methyl)
    2'-fluoro
    2'-amino
    2'-deoxy
    3'-deoxy
    3'-"label"
    3'-fluoro
    3'-amino
    3'-azido
    2',3'-unsaturated Combinations of base and sugar modifications Phosphate Modifications
    Phosphorothioate
    Phosphorodithioate
    Hydrogen phosphonate
    Methyl phosphonate
    Phosphotriester
    Phosphoramidite
    Methylene bridge derivatives Modified backbones
Polyamide nucleic acid (PNA) modified to give the equivalent of a 5' hydroxyl, e.g. having the formula

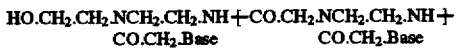

(For polyamide nucleic acids (PNA) see P. E. Neilsen, Science Volume 254, Dec. 6, 1991, Reports pages 1497–1500). Anti-sense and anti-gene oligonucleotides provide another example of nucleoside analogues.

The preferred and most important nucleoside analogues with which the invention is concerned are the four 2',3'-dideoxynucleosides ddA, ddC, ddG and ddT.

The term nucleoside adduct refers to a compound which results from the interaction between reactive entities and DNA or RNA. Such reactive entities include carcinogenic compounds or their metabolites and free radicals generated by electromagnetic radiation. High sensitivity detection of nucleoside adducts is of great importance in the evaluation of exposure of organisms to agents which modify nucleic acids. Examples of nucleoside adducts include the reaction products of polycyclic aromatic hydrocarbons (PAH) at N2 of guanosine, aromatic amines and oxygen radicals at C8 of guanosine, of alkylating agents at N7 and O6 of guanosine, and of mycotoxins at N7 of guanosine.

A preferred enzyme for use in the method is a polynucleotide kinase enzyme (PNK) such as T4 polynucleotide kinase. This enzyme is widely used in the preparation of $^{32}$P 5'-dNMP, under standard reaction conditions of 37° C. at pH 8.5, by a reaction which involves the phosphorylation of 3'-dNMP with [gamma$^{32}$P]-ATP and PNK. The inventors attempt to phosphorylate 2',3'-dideoxyadenosine (which lacks 3'-phosphate) with [gamma$^{32}$P] ATP, using this enzyme and these reaction conditions, was not successful. Success can surprisingly however be achieved using lower temperature and/or lower pH conditions. The preferred temperature range is 4°–30° C. with 18° to 30° C. being more preferred. The preferred pH range is 4.0–9.0. A high salt content, e.g. up to 150 mM NaCl, may be useful to promote the desired reaction. Incubation of the reactants under these conditions for times ranging from 10 minutes to 24 hours can give rise to good yields which increase with longer reaction times. The use of phosphatase free T4 PNK in which the 3' phosphatase activity has been substantially removed may be advantageous in eliminating side reactions which reduce the nucleoside monophosphate yields.

Another enzyme that can be used in the method of the invention is a phosphotransferase enzyme extracted from barley seedlings (J. Biol. Chem., 257, No. 9, pp 4931–9, 1982). The enzyme has two activities: one is the phosphotransferase which will transfer the phosphate from a nucleoside-5'-monophosphate to the 5'-hydroxyl group of any other nucleoside, with a preference for purine deoxynucleoside phosphate acceptors. The enzyme has not, so far as is known, been previously used in phosphorylating 2',3'-dideoxynucleosides. The other activity of this enzyme is that the phosphoryl-enzyme intermediate can transfer the phosphate to water rather than the nucleoside acceptor, creating inorganic phosphate. It is possible to control the enzyme activity by varying pH, the ratio of donor to acceptor, and the addition of salts to remove the water available to the enzyme. Preferred conditions of use are 5° to 30° C. at pH 4 to 9, particularly 7 to 8.5. The method requires the introduction of 5'-NMP which is then used as the phosphate donor. 5'-UMP is the preferred 5'-NMP.

Yet another phosphotransferase enzyme is derived from calf thymus.

A nucleotide analogue is a nucleoside analogue that has at least one 5'-phosphate or 5'-thiophosphate group.

Nucleotide phosphate and thiophosphate donors are well known in the field. Preferred examples of nucleotide phosphate donors are ATP, 5'-UMP, ATP-gammaS, 5'-UMP-αS. These donors may be radiolabelled with $^{32}$P, $^{33}$P and $^{35}$S so that the label transfers with a phosphate or thiophosphate group to the nucleoside analogue. A preferred nucleotide phosphate donor is [gamma$^{32}$P] ATP. Reaction of this donor with a 2',3'-dideoxynucleoside using PNK, gives rise to a 5'-[α$^{32}$P]nucleoside monophosphate.

These nucleoside monophosphates can be readily and efficiently converted by known means to the corresponding triphosphate. By the use of $^{33}$P or $^{35}$S, the corresponding [α$^{33}$P] or [α$^{35}$S]dideoxynucleoside triphosphates can be made.

When using an enzyme to phosphorylate a nucleoside, it has been usual and useful to provide a large excess of the chosen nucleotide phosphate (or thiophosphate) donor, which has the effect of pushing the reaction in the desired direction. When the nucleotide phosphate (or thiophosphate) donor is radiolabelled, it is not practicable to provide a large excess. As a result, the reaction conditions are more critical if a good yield of a desired radiolabelled nucleotide is to be obtained.

In another aspect, this invention provides a kit for sequencing nucleic acids which kit comprises a supply of each of the four chain terminating nucleotide or nucleotide analogue labelled with a radioisotope. Preferably the kit comprises [α$^{32}$P] and/or [α$^{33}$P] and/or [α35S] chain terminating nucleotide analogues e.g. dideoxynucleoside triphosphates together with a polymerase enzyme e.g. a T7 DNA polymerase, a supply of each of the four dNTPs and a buffer containing Mn$^{2+}$. The provision of the labelled ddNTPs should make their use in sequencing reliable with improved accuracy through reduced background and more even band intensity.

In another aspect the invention provides a method of sequencing a nucleic acid by a chain-termination technique, which method comprises effecting template-directed enzymatic synthesis using as a chain terminator a nucleotide or nucleotide analogue labelled with a radioisotope and detecting products of enzymatic synthesis by means of the radioisotope.

In yet another aspect, the invention provides any one of ddCTP and ddGTP and ddTTP which is radiolabelled by $^{32}$P or $^{33}$P or $^{35}$S wherein the radiolabel is preferably present in an α-phosphate group.

The detection of chain-termination DNA sequencing products after separation by gel electrophoresis has been achieved in any of several ways. The original methods involved the use of [α-$^{32}$P] dATP to internally-label the newly-synthesised DNA. Similarly, radiolabelled oligonucleotide sequencing primers can also be used. More recently, primers and nucleotides labelled with fluorescent dyes have also been used with expensive, sensitive instruments which detect the fluorescent products. These methods work well only if care is taken to ensure that all the DNA chains are correctly terminated by dideoxy-nucleotides. Any chains which terminate with deoxy-nucleotides at the 3' end may contribute to background signal in the final electrophetogram. Such terminations can occur when the polymerase is not highly processive or when the template contains strong secondary structures. Such non-specific stops are commonly seen in sequencing experiments and usually result in either errors or require re-sequencing to correctly assign the affected bases.

There have also been several successful methods using fluorescent dyes attached to the chain-terminating dideoxynucleoside (Prober et al, Lee, L G, Connell, C R , Woo, S L, Cheng, R D, McArdle, B F, Fuller, C W, Halloran, N D & Wilson, R K, (1992), Nucleic Acids Res., 20, 2471–2483.) These methods have the advantage that the label is directly attached to the molecule which causes chain-termination. The false or background terminations, when they occur, will not be detected by the fluorescence-detection instrument. There are two drawbacks to these methods. One is that the dye-tagged dideoxynucleoside triphosphates are not generally as efficient substrates for DNA polymerases as non-tagged dideoxynucleotides. They must be used at relatively high concentrations, and their rates of reaction vary with local sequence context giving rise to much less uniform band (or peak) intensities than non-tagged nucleotides. The second is that the equipment used to detect fluorescent-tagged DNA is complex and expensive compared with the equipment needed for traditional autoradiographic detection.

This invention features the benefits of placing the detectable label on the chain-terminating nucleotide without the drawbacks of expensive detection equipment or reduced reactivity with DNA polymerase. This is done by tagging the chain-terminating nucleotides with radioactive isotopes, especially of sulphur or phosphorus. This requires the efficient production of all four labelled dideoxynucleoside triphosphates and also requires a workable method to use them.

The original DNA polymerase used for chain-termination DNA sequencing (the large fragment of E. coli DNA polymerase I or Klenow enzyme) uses dideoxynucleotides relatively inefficiently. Most sequencing methods using this polymerase require the use of dideoxynucleotides at concentrations up to 50 or 100 times higher than the concentration of the corresponding deoxynucleotide. Expressed as a concentration ratio, ddNTP:dNTP is as high as 100:1. The typical minimum amount of dNTP for practical sequencing is on the order of 30 pmol each to allow extension of 0.5 pmol of primed template by an average of 240 bases. Thus, 3000 pmol of ddNTP may be required for sequencing with Klenow polymerase. The minimum specific radioactivity for detection of extension products from 0.5 pmol of template DNA with X-ray film and overnight exposure is approximately 500 Ci/mol. While this is practical for ordinary sequencing methods with non-labelled ddNTPs, the high amounts required make sequencing with labelled ddNTPs and this polymerase prohibitively expensive, wasteful and hazardous, requiring as much as 1.5 mCi per lane of sequence.

A key feature of the new sequencing method is the use of a DNA polymerase which efficiently uses dideoxynucleoside triphosphates so that the concentration ratio (and hence amount required) is reduced to practical levels. One such polymerase is modified T7 DNA polymerase when used in the presence of $Mn^{2+}$ (Tabor and Richardson, J. Biol. Chem. 264, 6447–6458). With this polymerase, dideoxynucleoside triphosphates react almost as efficiently as deoxynucleoside triphosphates, allowing the use of a concentration ratio of ddNTP:dNTP of 1:100. This ratio is 10,000 times more favourable for efficient use of dideoxynucleotides than the ratio for Klenow polymerase. With this polymerase and the amounts of template outlined above, as little as 0.3 pmol or 0.15 µCi of labelled dideoxynucleoside triphosphate will be required for each lane of the sequencing experiment. This amount is readily used economically and safely. Other DNA polymerase enzymes which make efficient use of didoexynucleoside triphosphates can also be used for this sequencing method.

An additional benefit when using modified T7 DNA polymerase and $Mn^{2+}$ is the uniform band intensities obtained. This makes interpretation of the sequencing experiment more accurate.

The following examples illustrate the invention.
T4 Polynucleotide Kinase=5'-dephosphopolynucleotide 5'-phosphotransferase EC 2.7.1.78

Polynucleotide kinase 3' phosphatase free=5'-dephosphopolynucleotide 5'-phosphotransferase EC 2.7.1.78—from T4 am N81 pse T1 phage infected *E. coli* BB

EXAMPLE 1

3.5 µmoles of each 2',3'-dideoxynucleoside (all four bases) were individually mixed with 50 units of 3'-phosphatase free PNK and 5 nmoles of [gamma$^{32}$P] ATP in a buffer containing 50 mM Tris-HCl pH 7.5, 2.5 mM DTT and 30 mM Mg Acetate, 150 mM NaCl, 0.1 mM Spermine and 0.5 mM NH$_4$Cl. The final reaction volumes were 100 µl and the reactions were incubated at 18° C. The reactions were followed by TLC analysis on PEI cellulose plates developed in 0.5M LiCl and 1M formic acid.

Table 1 shows the Conversions to [$^{32}$P]ddNMP's with time.

TABLE 1

| TIME (minutes) | % [$^{32}$P] ddAMP | % [$^{32}$P] ddCMP | % [$^{32}$P] ddGMP | % [$^{32}$P] ddTMP |
|---|---|---|---|---|
| 30 | 44.1 | 33.6 | 12.7 | 28.8 |
| 90 | 64.3 | 83.3 | 26.7 | 76.6 |

The TLC system was calibrated by using $^{32}$PO$_4$, [$^{32}$P] ddAMP (produced chemically) and 5'dAMP as markers. This enabled the TLC plates to be interpreted and the peaks, obtained using a beta-particle scanner, identified.

EXAMPLE 2

The [32P]ddNMP products from Example 1 were synthesised on a larger scale.

35 µmoles of each 2',3'-dideoxynucleoside (all four bases) were individually mixed with 500 units of 3'phosphatase free PNK and 75 mCi (25 nmoles) of [gamma$^{32}$P] ATP in a buffer containing 50 mM Tris-HCl pH 7.5, 2.5 mM DTT, 30 mM Mg Acetate, 150 mM NaCl, 0.1 mM Spermine and 0.5 mM NH$_4$Cl. The final reaction volumes were 2 ml and the reactions were incubated at 18° C. for 2 hours. The reactions were followed by TLC analysis on PEI cellulose plates developed in 0.5M LiCl and 1M formic acid.

After 2 hours the reactions were stopped by the addition of 2 ml absolute ethanol. After filtration the reactions were purified by HPLC ion-exchange chromatography. TLC analysis of the purified monophosphates showed that the [$^{32}$P]ddAMP contained some inorganic $^{32}$PO$_4$. The other three monophosphates all had purities in excess of 90%. The yields of the reactions were of the same order as those seen in the small scale assays in Table 1.

The [$^{32}$P]ddNMP's were converted to the respective [α$^{32}$P]ddNTP's readily and efficiently by standard methods.

After purification by HPLC ion-exchange chromatography the [α$^{32}$p] ddNTP's were resuspended at ≈4 mCi/ml in aqueous solution. The final yields from [gamma$^{32}$P] ATP were:

ddATP 48%
ddCTP 46%
ddGTP 15%
ddTTP 24%

Samples were taken for identification by analytical HPLC against the respective non-radioactive ddNTP marker and for use in DNA sequencing. The results showed that with all four ddNTP's the radiolabelled [α$^{32}$P]ddNTP and the non-radioactive ddNTP eluted from the HPLC column at exactly the same time. Also in the absence of any other terminator or radiolabel, apart from that synthesised above, the sequence of an M13 template was successfully determined when compared to the sequence produced using [α$^{35}$S] dATP internal label and non-radioactive ddNTP's.

This proves that the [α$^{32}$P] ddNTP's were made and therefore that PNK can, under these conditions, phosphorylate 2',3'-dideoxynucleosides.

EXAMPLE 3 BARLEY SEEDLING PHOSPHOTRANSFERASE 0.5 µmoles of uridine-5'-monophosphate (5'-UMP) was mixed individually with 0.5 µmoles of each 2',3'-dideoxynucleoside (except 2',3'-ddG which was 0.15 µmoles of 5'-UMP and 2',3'-ddG due to solubility problems with 2',3'-ddG—note still in 1:1 mole ratio) and 10 µl Barley Seedling Phosphotransferase (1.3 units/ml) in 50 mM Tris-HCl pH 7.5, 1 mM MgCl$_2$ and 0.002% Triton-100. The final reaction volume was 50 μl and the reaction was incubated at 25° C. for 4 hours. 15 μl samples were removed for analysis by ion-exchange chromatography, the samples were made up to 120 μl with water prior to loading. Analysis by this method showed that all 4 base 2',3'-dideoxy nucleoside-5'-monophosphates had been successfully made.

A second experiment, this time using 5'-UMP spiked with [$^{32}$P] 5'-UMP, under the same conditions as above except using a 5'-UMP: 2',3'-dideoxyadenosine mole ratio of 24:1, gave a radiolabelled peak of 2',3'-dideoxyadenosine-5'-monophosphate on an analytical HPLC system which exactly matched that produced by the PNK method. The HPLC system was calibrated using a mixture of non-radioactive 5'-UMP and 5'-dAMP (no ddAMP available commercially). These were shown to be well separated by the system with the 5'-dAMP running slightly slower than the [$^{32}$P] 2',3'-dideoxyadenosine-5'-monophosphate, which is to be expected on an ion-exchange system due to the 3'-OH group. When this reaction was repeated at pH 5.0 in 50 mM sodium acetate buffer the HPLC analysis revealed a very fast running radiolabelled peak that was identified as inorganic phosphate. This showed that the reaction is pH dependent. The addition of high concentrations of salt may also be beneficial and increase the yield of monophosphate produced by inhibiting the production of inorganic phosphate.

EXAMPLE 4 SEQUENCING PROTOCOL

Sequencing was carried out using the Sequenase Version 2.0 kit from US Biochemical Co., Cleveland, Ohio.

1 μl (0.5 pmol) Primer, 2 μl reaction buffer, 5 μl (1 μg) control template and 2 μl water were mixed in a clean sterile vial. This was heated to 65° C. for 2 minutes and then slowly cooled to 30° C. To this was added 1 μl DTT (0.1M) solution, 2 μl extension labelling mix (diluted 1:5), 1 μl Mn$^{++}$ buffer, 2 μl Sequenase DNA polymerase (diluted 1:8) and 0.5 μl water (this was replaced by 0.5 μl [α$^{35}$S] dATP in the internally labelled control, this also used the standard termination mix and not the one listed below). This was left at room temperature for 5 minutes. 1 μl of a mix of all 4 dNTP's (either 30 μmolar or 480 μmolar solution), 1 μl of the relevant [α$^{32}$P] ddATP dilution (containing a range of specific activity dilutions with a varying chemical content of 0.3, 4.8 or 48 pmoles. The ddNTP:dNTP ratio was varied between 1:10 and 1:100) and 0.5 μl water was added to 3.5 μl of the above solution. This was incubated at 37° C. for 5 minutes and then 4 μl of stop dye was added to each reaction tube. All the reaction tubes were heated at 70°–80° C. for 5 minutes. 4 μl of each reaction was loaded onto a standard 6% polyacrylamide sequencing gel that had been pre-run for 40 minutes. The gel was run at 45 mA until the first dye had run off the gel, ≈ 2 hours. The gel was then dried before exposure to film Amersham Hyperfilm MP overnight. The results showed a much improved sequencing track with low background and even band intensities.

EXAMPLE 5 PHOSPHORYLATION OF 2'-DEOXYADENOSINE 0.3 mgs of 2'-deoxyadenosine were mixed with 30 units of T4 PNK and 8 nmoles of [gamma$^{32}$P] ATP in 50 mM Tris-HCl pH 7.5, 5 mM DTT and 14 mM MgCl$_2$. The final reaction volume was 100 μl and the reaction was incubated at 24° C. The reaction was followed using the same TLC system as in Example 1.

The results showed that the incorporation to [$^{32}$P] 5'dAMP was

Time 45 minutes=4%
Time 240 minutes=15%
Overnight=44%

EXAMPLE 6 (THIOPHOSPHORYLATION)

3.5 μmoles of 2',3'-dideoxyadenosine, adenosine and 2'deoxyadenosine were individually mixed with 150 units 3' phosphatase free PNK and 85 pmoles of [gamma$^{35}$S] ATP in a buffer containing 50 mM Tris-HCl pH 7.5, 2.5 mM DTT, 20 mM Mg Acetate, 0.1 mM Spermine and 0.5 mM NH$_4$Cl. The final reaction volumes were 100 μl and the reactions were incubated at 18° C. The reactions were followed by TLC analysis on PEI cellulose plates developed in 0.5M LiCl and 1M formic acid.

After a 21 hour incubation the reactions contained 8.3% Adenosine-5'-monothiophosphate [$^{35}$S]

11.2% 2'-deoxyadenosine-5'-monothiophosphate [$^{35}$S]

2.8% 2',3'-dideoxyadenosine-5'-monothiophosphate[$^{35}$S]

EXAMPLE 7 (MODIFIED SUGARS)

3.5 μmoles of 3'-azidothymidine was mixed with 50 units 3' phosphatase free PNK and 5 nmoles of [gamma$^{32}$P] ATP in a buffer containing 50 mM Tris-HCl pH 7.5, 2.5 mM DTT, 20 mM Mg Acetate, 0.1 mM Spermine and 0.5 mM NH$_4$Cl. The final reaction volume was 100 μl and the reaction was incubated at 18° C. The reaction was followed by TLC analysis on PEI cellulose plates developed in 0.5M LiCl and 1M formic acid.

After a 3 hour incubation the reaction contained 22% 3'-azidothymidine-5'-monophosphate [$^{32}$P].

EXAMPLE 8 (BASE MODIFICATIONS)

3.5 μmoles of 7-deazaadenosine (tubercidin), 3-nitropyrole nucleoside and 5-nitroindole nucleoside (ref: D Loakes and D M Brown, NAR, 1994, Vol. 22, No. 20, pg 4039–4043) were individually mixed with 50 units 3' phosphatase free PNK and 5 nmoles of [gamma$^{32}$P] ATP in a buffer containing 50 mM Tris-HCl pH 7.5, 2.5 mM DTT, 20 mM Mg Acetate, 0.1 mM Spermine and 0.5 mM NH$_4$Cl. The final reaction volumes were 100 μl and the reactions were incubated at 18° C. The reactions were followed by TLC analysis on PEI cellulose plates developed in 0.5M LiCl and 1M formic acid.

After a 3 hour incubation additional peaks were observed on the TLC scans. These were presumably due to the substrate as they were not seen in the absence of substrate.

63.0% 7-deazaadenosine-5'-monophosphate [$^{32}$P]*

16.1% 3-nitropyrolenucleoside-5'-monophosphate [$^{32}$P]*

23.9% 5-nitroindolenucleoside-5'-monophosphate [$^{32}$P]*

\* These products were only seen in the presence of the substrate and were not seen in the control experiments without substrate.

EXAMPLE 9

3.5 μmoles of each 2',3'-dideoxynucleoside (all four bases) were individually mixed with 1000 units 3'phosphatase free PNK and 60 to 100 mCi of [gamma$^{33}$P] ATP (at ≈3000 Ci/mmole) in a buffer containing 50 mM Tris-HCl pH 7.5, 2.5 mM DTT, 20 mM Mg acetate, 150 mM NaCl, 0.1 mM spermine and 0.5 mM NH$_4$Cl. The final reaction volumes were 2 ml and the reactions were incubated at 18°

C. from 2 to 6 hours. The reactions were followed by TLC analysis on PEI cellulose plates developed in 0.5M LiCl and 1M formic acid.

The reactions were stopped by the addition of 2 ml absolute ethanol. After filtration the reactions were purified by HPLC ion-exchange chromatography. TLC analysis of the purified monophosphates showed that the [$^{33}$P]ddAMP contained some inorganic $^{33}$PO$_4$. The other three monophosphates all had purities in excess of 90%. The yields of the reactions were of the same order as those seen in the small scale assays in Table 1.

The [$^{33}$P] ddNMP's were converted to the respective [$\alpha^{33}$P] ddNTP's readily and efficiently by standard methods.

After purification by HPLC ion exchange chromatography the [$\alpha^{33}$P] ddNTP's were resuspended at ≈4 mCi/ml in aqueous solution. The final yields from [gamma$^{33}$P] ATP were:

ddATP 40%
ddCTP 30%
ddGTP 20%
ddTTP 16%

Samples were taken for identification by analytical HPLC against the respective non-radioactive ddNTP marker and for use in DNA sequencing. The results showed that with all ddNTP's the radiolabelled [$\alpha^{33}$P] ddNTP and the non-radioactive ddNTP eluted from the HPLC column at exactly the same time.

EXAMPLE 10 SEQUENCING DNA

Using the methods outlined in Examples 1–3, [$\alpha$-$^{32}$P] ddGTP, [$\alpha$-$^{32}$P] ddATP, [$\alpha$-$^{32}$P] ddTTP and [$\alpha$-$^{32}$P] ddCTP were prepared with a specific activity of approximately 2000 Ci/mmol and concentration of 0.5 µM. These were used in the following fashion to determine the base sequence of M13mp18 DNA. Many of the reagents described here can be found in the Sequenase DNA sequencing kits produced by US Biochemical Co., Cleveland, Ohio.

Four nucleotide termination mixes were prepared by mixing 2 µl of 15 µM dATP, dTTP, dCTP, dGTP and 100 mM NaCl with 0.6 µl (containing 0.3 pmol) of each of the radiolabelled ddNTP solutions.

Template DNA (M13mp18, 1.0 µg in 5 µl) was mixed with 0.5 pmol (1 µl) of M13 "–40"23-mer oligonucleotide primer, 1 µl of MOPS buffer (400 mM morpholinopropane-sulphonic acid-NaOH, pH 7.5, 500 mM NaCl, 100 mM MgCl$_2$, 1 µl of Mn buffer, 50 mM MnCl$_2$, 150 mM Isocitrate, sodium salt) and 2 µl of water for a total volume of 10 µl. This mixture was warmed to 37° C. for 10 min to anneal the primer to the template. The mixture was chilled on ice and 1 µl of 0.1M dithiothreitol and 2 µl of polymerase mixture (1.6 Units/µl Sequenase Version 2.0 T7 DNA polymerase (U.S. Biochemical Corp.), 2.0 Units/ml inorganic pyrophosphotase 20 mM Tris.HCl pH 7.5, 2 mM DTT 0.1 mM EDTA, 50% Glycerol) added and mixed well. Then 3 µl portion of this DNA and polymerase mixture were mixed with the pre-warmed (to 37° C.) termination mixtures 2.6 µl) described above. The mixtures were allowed to incubate for 10 min at 37° C., then 4 µl of stop solution (95% Formamide 20 mM EDTA 0.05% Bromophenol Blue 0.05% Xylene Cyanol FF) were added to stop the reaction.

The mixtures were heated briefly and applied to a denaturing polyacrylamide electrophoresis gel buffered with Tris-taurine-EDTA buffer (U.S. Pat. No. 5,134,595, Pisar-Williamson, D. & Fuller, C. W. (1992) Comments 19, 29–36). After electrophoresis, the gel was dried by standard procedures and exposed to film overnight. The resulting DNA sequencing autoradiogram was exceptionally free of background, clearly showed the identity of the first nucleotide added to the 3' end of the primer, had uniform band intensities.

EXAMPLE 11 SEQUENCING USING dITP TO ELIMINATE COMPRESSION ARTIFACTS

Compression artifacts occur when the DNA being separated on a sequencing electrophoresis gel are not completely denatured. Nucleotide analogues such as dITP (deoxyinosine triphosphate) which replace dGTP in the sequencing reactions can eliminate compression artifacts (Tabor, S. and Richardson, C. C. (1987) Proc. Nat. Acad. Sci. USA 84, 4767–4771). Sequencing reactions were run exactly as described in Example 10 except that the four nucleotide termination mixes were prepared by mixing 2 µl of 75 µM dITP, 15 µM dATP, dTTP, dCTP and 100 mM NaCl with 0.6 µl (containing 0.3 pmol) of each of the radiolabelled ddNTP solutions. Sequencing of M13mp18 template DNA was done using a different primer chosen to sequence through a region prone to compression artifacts. When the dITP-containing mixture was used, no compression artifacts were observed while control sequences run with dGTP mixtures did have compressed, unreadable regions.

We claim:

1. A method of making a nucleotide, nucleotide analogue, or nucleotide adduct, having a 5=-phosphate or a 5'-thiophosphate group said method comprising reacting a starting nucleoside, nucleoside analogue, or nucleoside adduct having a 5'-OH group but no 3'-phosphate group, with a nucleotide phosphate donor or nucleotide thiophosphate donor in the presence of an enzyme which catalyses the reaction.

2. A method as claimed in claim 1 wherein the nucleotide phosphate donor or nucleotide thiophosphate donor is radiolabelled with a radioisotope selected from the group consisting of $^{32}$P, $^{33}$P, and $^{35}$S, whereby the obtained nucleotide, nucleotide analogue, or nucleotide adduct is radiolabelled at the 5'-phosphate or 5'-thiophosphate group with $^{32}$P, $^{33}$P, or $^{35}$S.

3. A method as claimed in claim 1 wherein the starting nucleoside analogue is a 2',3'-dideoxynucleoside.

4. A method as claimed in claim 1 wherein the starting nucleoside analogue is selected from the group consisting of 3'-fluoro, 3'-amino, and 3'azido nucleosides, polyamide nucleic acids and an anti-sense oligonucleotide.

5. A method as claimed in claim 1 wherein the enzyme is a polynucleotide kinase.

6. A method as claimed in claim 1 wherein the reaction is performed at 4°–30° C. and pH 4–9.

7. A method as claimed in claim 1 wherein the nucleotide phosphate donor or nucleotide thiophosphate donor is selected from the group consisting of gamma$^{32}$P-ATP, gamma$^{35}$S-ATP, and gamma$^{33}$P-ATP.

8. A method as claimed in claim 1 wherein a 2'-3'-dideoxynucleoside is reacted with gamma$^{32}$P-ATP to make a 5'-$^{32}$P nucleoside monophosphate.

9. A method as claimed in claim 8, wherein the 5'-$^{32}$P nucleoside monophosphate is subsequently converted to the di- or tri-phosphate.

10. A method as claimed in claim 1 wherein the enzyme is a phosphotransferase enzyme derived from barley seedlings.

11. A kit for sequencing nucleic acids, which comprises each of the four chain terminating nucleotides or nucleotide analogues, wherein the chain terminating nucleotides or nucleotide analogues are labelled with a radioisotope.

12. A kit as claimed in claim 11, wherein the chain terminating nucleotides or nucleotide analogues are dideoxynucleotides.

13. A kit as claimed in claim 11 wherein each of the four chain terminating nucleotides or nucleotide analogues are labelled with a radioisotope selected from the group consisting of $^{32}$P, $^{33}$P, and $^{35}$S.

14. A kit as claimed in claim 11 wherein the kit further comprises a polymerase enzyme, deoxyadenosine triphosphate, deoxyguanosine triphosphate, deoxycytidine triphosphate, and deoxythymidine triphosphate.

15. A kit as claimed in claim 14, wherein the polymerase enzyme is a T7 DNA polymerase and the kit further comprises a buffer containing $Mn^{2+}$.

16. A method of sequencing a nucleic acid by a chain-termination technique, which method comprises effecting template-directed enzymatic synthesis using as a chain terminator, a nucleotide or nucleotide analogue labelled with a radioisotope and detecting products of enzymatic synthesis by means of the radioisotope.

17. A method as claimed in claim 16, wherein the enzymatic synthesis reaction is performed using a T7 DNA polymerase enzyme in the presence of all four dNTPs and of the labelled chain terminating nucleotide or nucleotide analogue in a buffer containing $Mn^{2+}$.

18. A method as claimed in claim 16 wherein the radioisotope is $^{32}$P or $^{33}$P or $^{35}$S.

19. A chain terminator selected from the group consisting of ddCTP, ddGTP and ddTTP which is radiolabelled with a member selected from the group consisting of $^{32}$P, $^{33}$P and $^{35}$S.

20. The chain terminator according to claim 19 wherein the radiolabel is present in an α-phosphate group.

* * * * *

UNITED STATES PATENT AND TRADEMARK OFFICE
CERTIFICATE OF CORRECTION

PATENT NO. : 5,702,925

DATED : December 30, 1997

INVENTOR(S) : Smith et al.

It is certified that error appears in the above-identified patent and that said Letters Patent is hereby corrected as shown below:

Column 3, line 65, "[α35S] should be --[$\alpha^{35}S$]--.

Column 10, line 27, "5=-phosphate" should be --5'-phosphate--.

Signed and Sealed this

Twelfth Day of September, 2000

Attest:

Q. TODD DICKINSON

*Attesting Officer*     *Director of Patents and Trademarks*